United States Patent
Mosemiller

(10) Patent No.: US 6,869,410 B1
(45) Date of Patent: Mar. 22, 2005

(54) COMPRESSION GARMENT FITTING DEVICE

(76) Inventor: Robert L. Mosemiller, 2084 Hanson St., Port Charlotte, FL (US) 33952

(*) Notice: Subject to any disclaimer, the term of this patent is extended or adjusted under 35 U.S.C. 154(b) by 267 days.

(21) Appl. No.: 10/207,359

(22) Filed: Jul. 30, 2002

(51) Int. Cl.⁷ .................................................. A61F 5/00
(52) U.S. Cl. ............................. 602/1; 602/41; 602/63; 602/75; 128/878
(58) Field of Search ......................... 602/1, 3, 41, 76, 602/77, 20, 21, 63, 75; 128/878, 879, 880; 2/16; 428/36.1, 36.9

(56) References Cited

U.S. PATENT DOCUMENTS

| | | | | |
|---|---|---|---|---|
| 2,571,946 A | * | 10/1951 | Rosenfield | 602/1 |
| 2,715,903 A | * | 8/1955 | Scholl | 602/1 |
| 2,739,587 A | * | 3/1956 | Scholl | 602/1 |
| 3,053,253 A | * | 9/1962 | Liloia et al. | 602/1 |
| 3,358,682 A | * | 12/1967 | Preston | 602/1 |
| 3,476,109 A | * | 11/1969 | Hurney | 602/1 |
| 5,540,652 A | * | 7/1996 | Callinan et al. | 602/1 |
| 5,540,964 A | * | 7/1996 | Mallen | 428/36.1 |
| 5,744,528 A | * | 4/1998 | Callinan et al. | 602/1 |

* cited by examiner

Primary Examiner—Fadi H. Dahbour
(74) Attorney, Agent, or Firm—Frank A. Lukasik

(57) ABSTRACT

A device for facilitating the fitting of compression bandages consisting of an essentially tubular arrangement of metal rods mounted to a ring base over which a compression bandage is stretched to allow a user to push an arm into the bandage for complete and efficient deployment of the bandage. A guide is provided to align the distal ends of the rods to engage the lock pins in the holes before mounting the bandage.

2 Claims, 11 Drawing Sheets

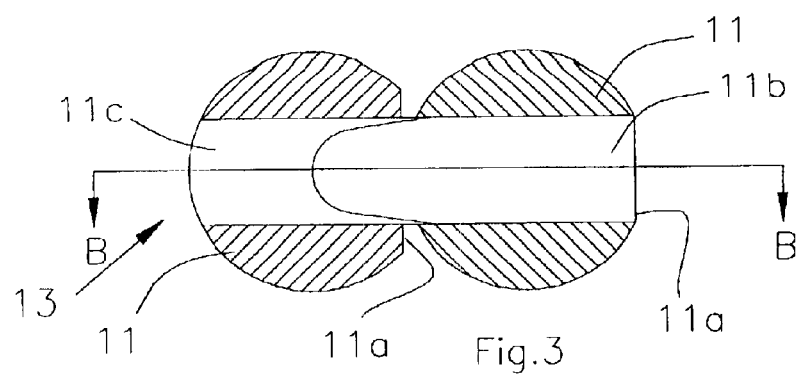
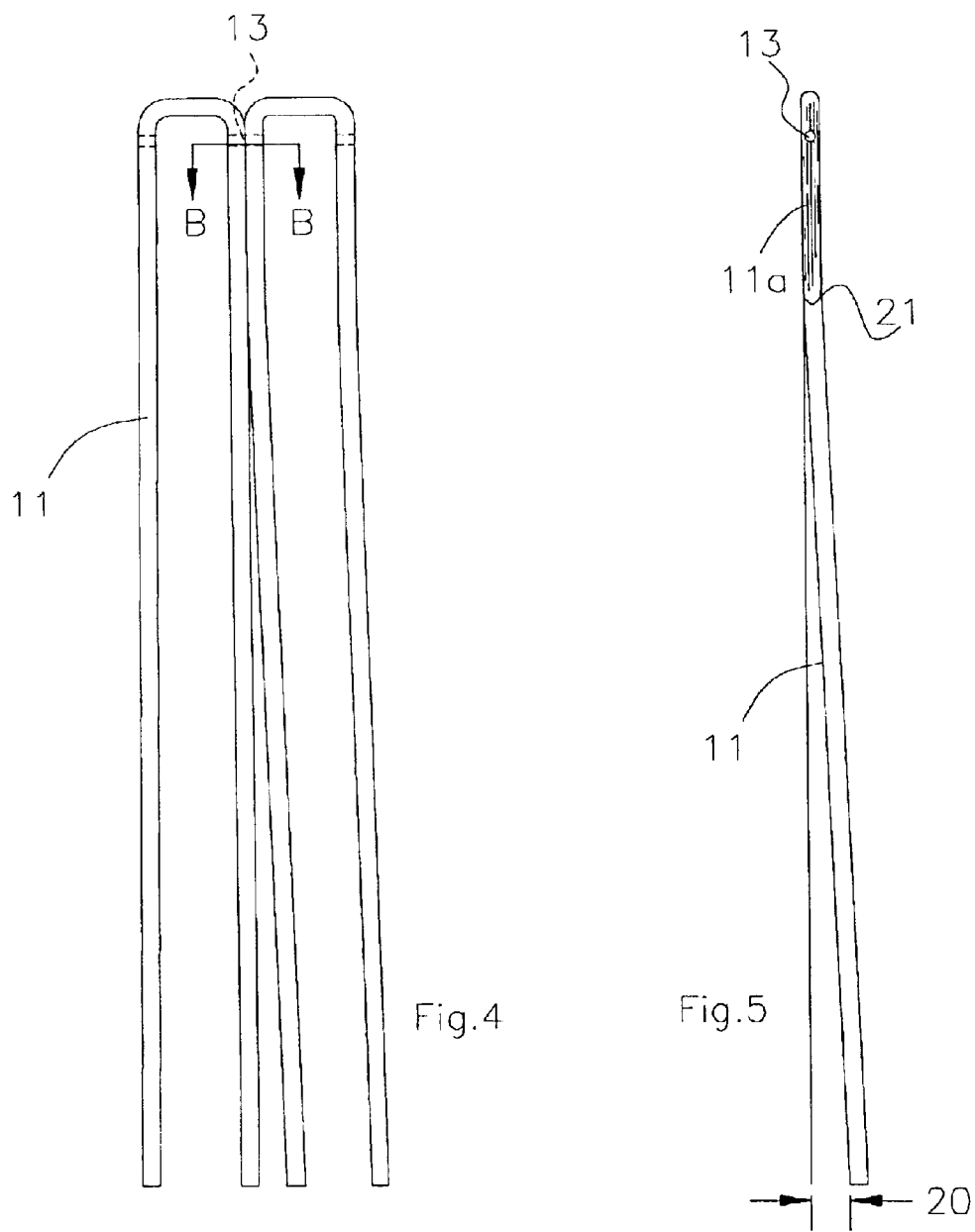

COMPRESSION GARMENT FITTING DEVICE

BACKGROUND OF THE INVENTION

This invention relates to devices facilitating the fitting of compression bandages and, more particularly, to an essentially tubular arrangement of metal rods mounted to a ring base over which a compression bandage is stretched allowing a user to push an arm into the bandage for complete and efficient deployment of the bandage.

Post-operatively, patients may be prone to edema which requires compression therapy to clear fluids from a limb and to thereafter prevent further fluid accumulation. A variety of compression bandages are available which provide differing degrees of compression, the most aggressive of which are difficult to install especially in the presence of swelling and when the patient attempts the installation alone. This is an important way of controlling swelling. The sleeve or stocking works by compressing the swollen tissues and preventing the fluid from building up. The support it provides allows the muscles to pump fluid away more effectively. The garments are designed so that more pressure is applied around the lower part of the limb to encourage the fluid to drain. Prior art devices include the use of plastic coated wire frames over which the bandage is stretched allowing the user to slide the arm through the bandage. The difficulty with such a device is an inability to overcome the friction of the arm against the bandage. The bandage concertinas over the frame and presents a series of ridges through which the arm must pass. The ridges present a formidable physical barrier to the arm, especially one that is swollen.

The present invention seeks to improve on prior art devices by providing a sturdy frame over which a compression bandage can be fitted and through which a patient's arm can be inserted. The frame of this device being composed of a plurality of "fingers", is sufficiently flexible to expand over the contours of the patient's arm and yet firm enough, when locked in place, to withstand the compression of even the most aggressive bandage. As compression treatment and maintenance may be protracted, a device is needed which will be durable and will last through the treatment period regardless of the aggressiveness of the bandage or the number of applications needed.

SUMMARY OF THE INVENTION

The present invention has an annular base into which a plurality of metal rods are affixed. The rods are each essentially "U" shaped at the top with legs extending a sufficient distance to provide coverage of a forearm—different sizes are made to accommodate those with smaller limbs. The bottoms of the rods are either welded in place or attached by some adhesive/epoxy medium. The top outer edge of each rod is flat and an arrangement of holes and pins are located thereupon, perpendicular to the axis of the rod. The rod ends fit into the holes such that the rods form a stable circular shape which remains throughout the mounting and deployment of a compression bandage. A circular guide is used to align the rods prior to the fitting of the bandage. When the guide is pushed down between the extending rods, they are correctly positioned to allow the holes/pins to align. When the guide is removed, the rods form a neat circular alignment awaiting the fitting of the bandage.

It is a fundamental object of the invention to facilitate the fitting of a compression bandage to a patient's arm by holding the bandage in an expanded form such that the arm may pass within the bandage with a minimum of friction and that the device may be thereafter removed with minimal effort and discomfort.

It is a further object of the invention to accommodate bandages of various sizes and strengths.

It is a further object of the invention to allow a patient to fit a compression bandage without the assistance of another.

It is a further object of the invention to be manufactured from durable materials, either metal, plastics, or a combination thereof.

BRIEF DESCRIPTION OF THE DRAWINGS

An illustration of a Prior Art device is shown.

FIG. 3 is a plan view in broken section of the hole/pin locking means of the device.

FIG. 4 is an elevational view of a pair of the invention rods, showing the location of the hole/pin locking means.

FIG. 5 is an elevational view of a single rod of the invention showing the vertical configuration of one of the invention rods, showing the location of the hole/pin locking means.

DETAILED DESCRIPTION OF A PREFERRED EMBODIMENT

Figure 1:
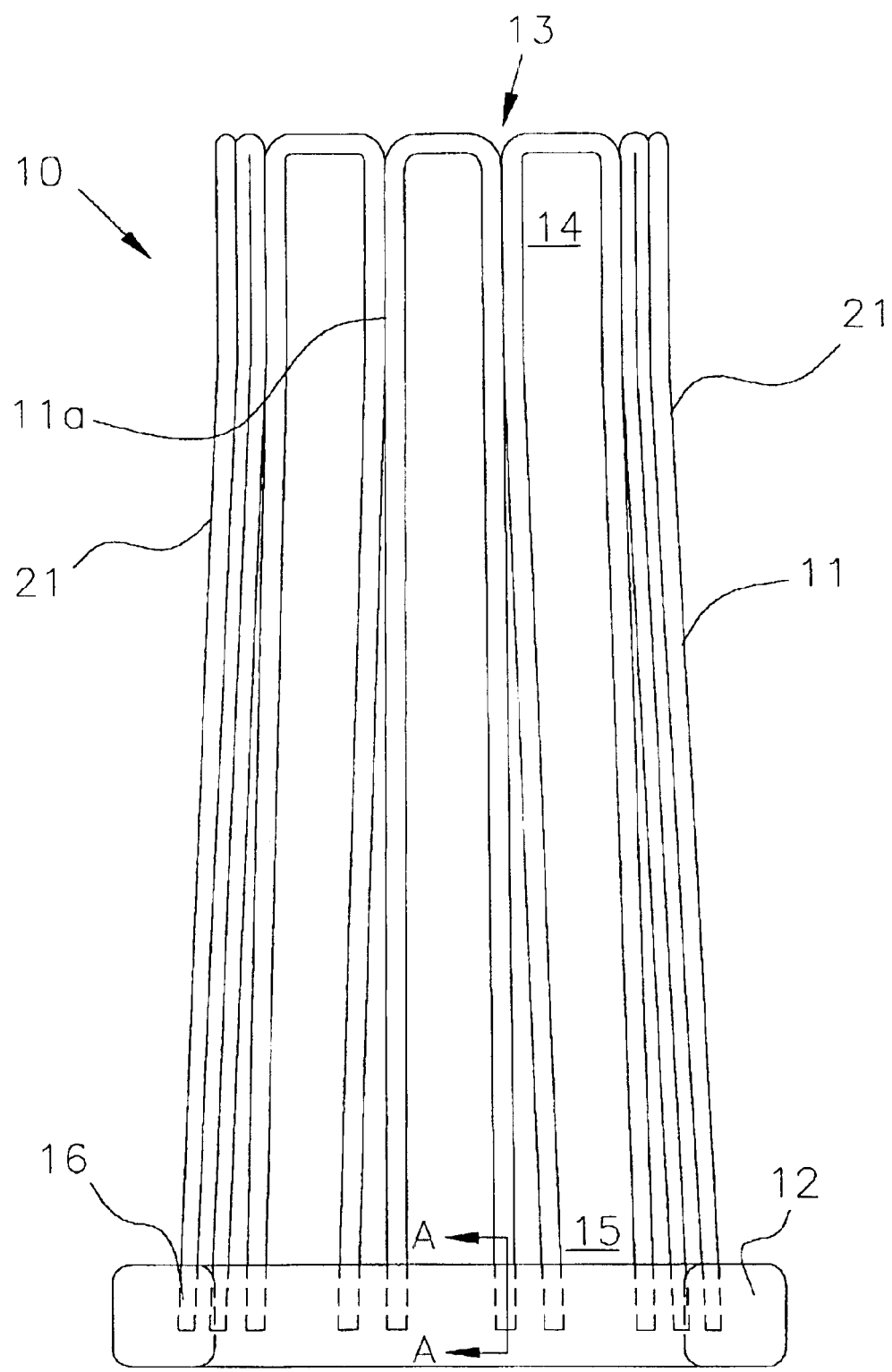
FIG. 1 is an elevational view, partially in section showing the device as described.

Referring now to the drawings wherein like numerals designate like and corresponding parts throughout the several views, the applicator of the invention is designated by the numeral 10. In FIG. 1, ring base 12 is fitted with rods 11. The rods 11 may be embedded in a ring base 12 made of plastic or wood or the rods 11 may be welded to a brass ring. In the preferred embodiment the rods 11 and the ring base 12 were made from brass. The rods 11 are bent at a slight angle 21, displacement 20, to provide vertical contact of flat surfaces 11a for aligning the rods at the top end. The flat surfaces 11a provide a greater contact surface than the normally round surface of the remainder of the rods 11.

Ten rods 11 have been found to be more effective than having fewer rods because it gives the compression sleeve more spaces to expand in both directions and puts less pressure on the arm. As shown in the drawing of the Prior Art, the bandage 22 is shown compressing the users arm as it is being applied.

Figure 2:
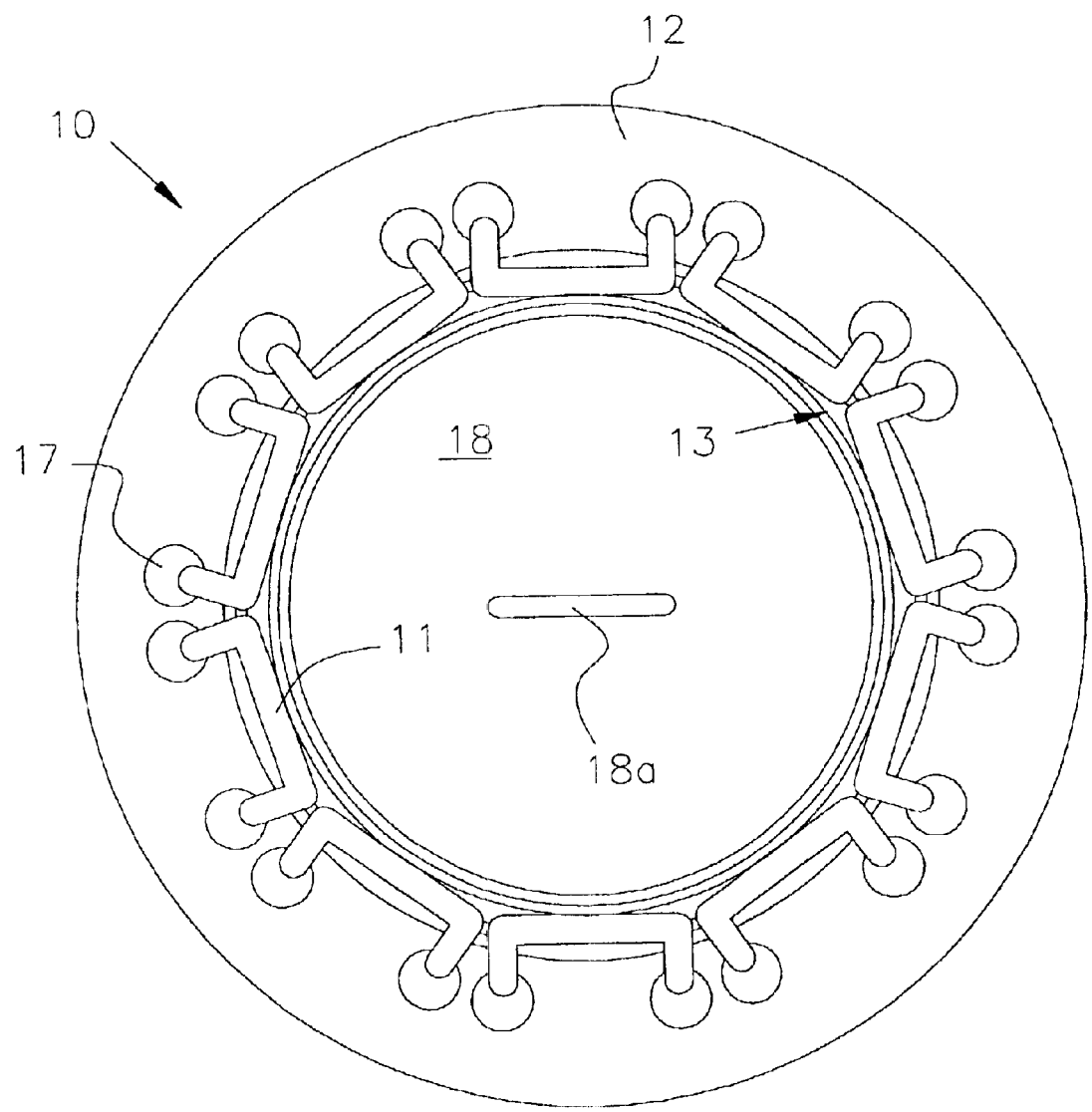
FIG. 2 is a plan view showing the device as described with the alignment guide in place.
Figure 6:
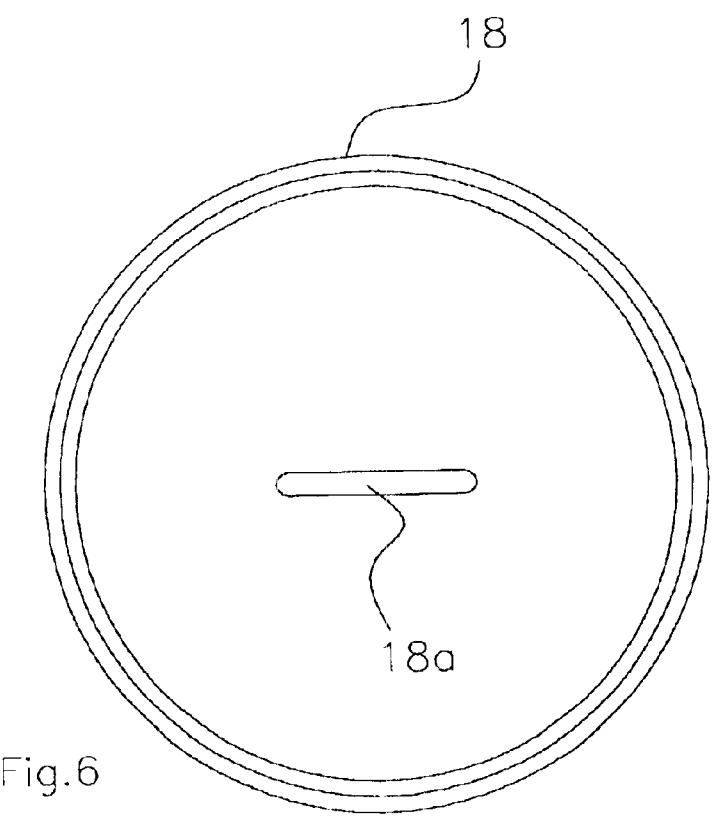
FIG. 6 is a plan view of the alignment means of the device.
Figure 9:
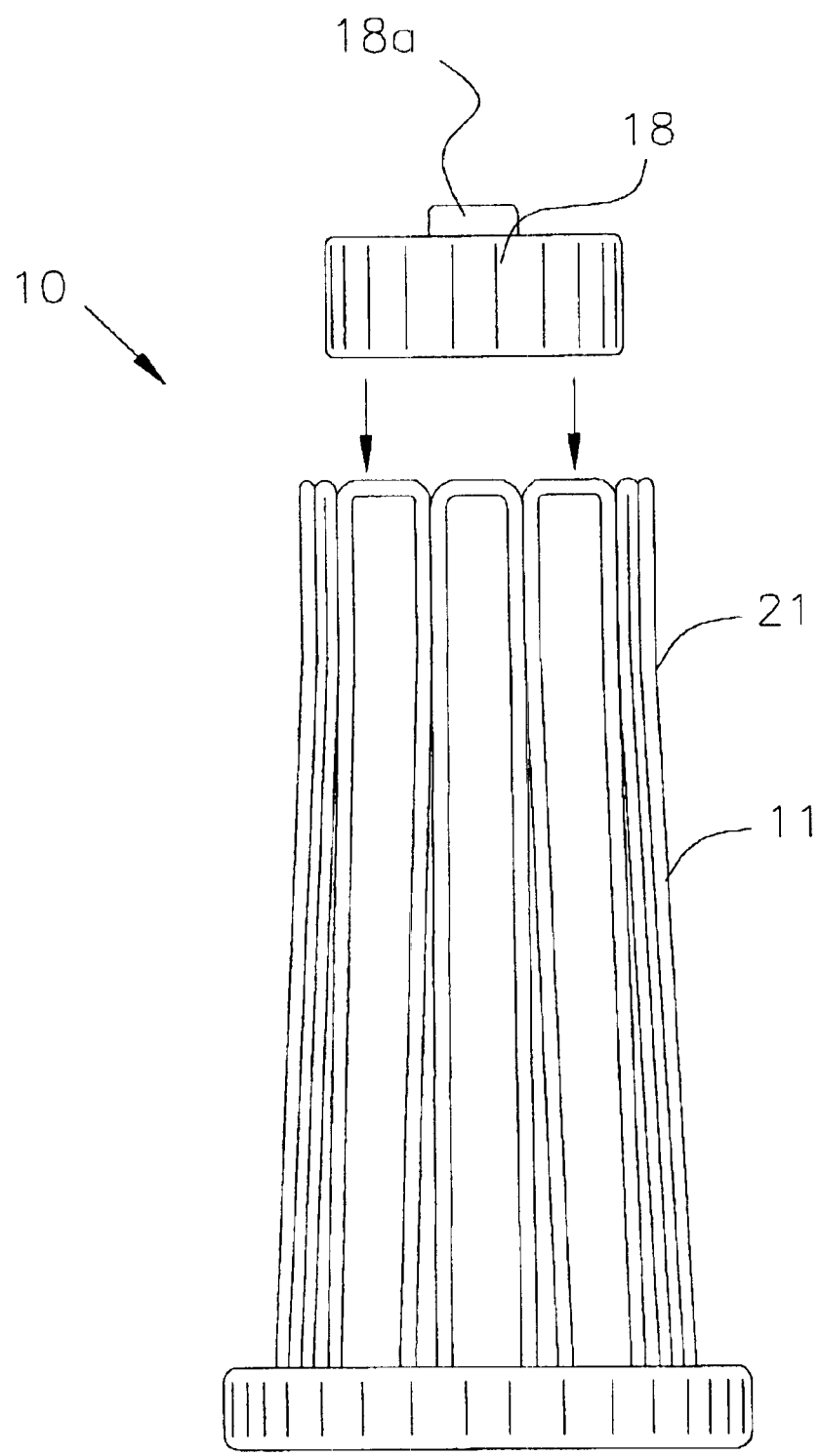
FIG. 9 is an elevational view of the device showing the deployment of the alignment means of the device prior to the fitment of a compression bandage.

Referring now to FIGS. 2 and 9, rods 11 are arranged to form a circle concentric with the base 12. FIG. 2 shows the guide 18 being pressed downwardly, thus spreading the outer surfaces of the rods 11. The guide 18 is then removed, and the rods 11 are permitted to contact adjoining rods 11 and the rod locking means 13 (lock pin 11b and hole 11c) are mated. Mating of the locking means 13 retains the rods 11 in a rigid, closed position when the bandage 22 is inserted over the applicator 10. The guide 18 has a handle 18a for gripping when in use.

Figures 7, 8:
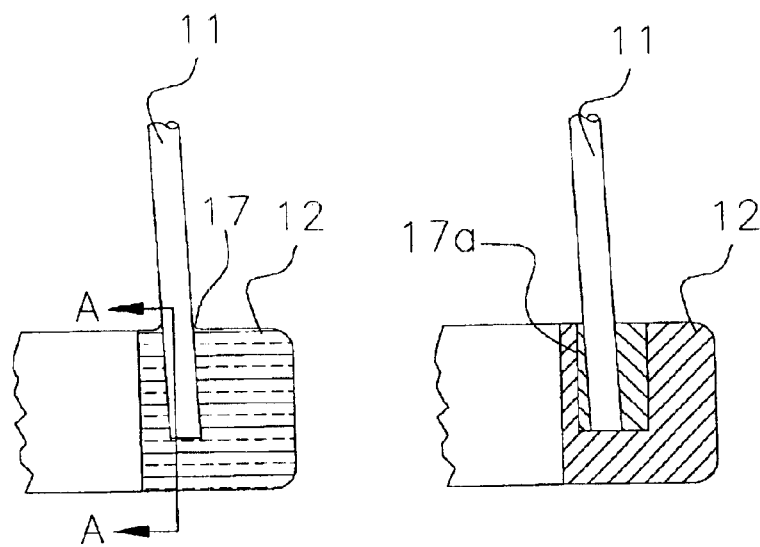
FIG. 7 is a sectional view of the annular base of the device showing the mounting of the device rods using welding.
FIG. 8 is a sectional view of the annular base of the device showing the mounting of the device rods using adhesive material.

FIGS. 7 and 8 show two alternative means for rods 11 to be attached to the ring base 12. In addition, a brass rod ring may be used to weld the rods 11 thereto.

FIG. 9 shows a typical deployment of guide 18. A guide 18 fits within the circular shape formed by the rods 11. The guide 18 is used to open the rod ends to align the lock pins 11b and the holes 11c formed in the flat surfaces 11a.

Figure 10:
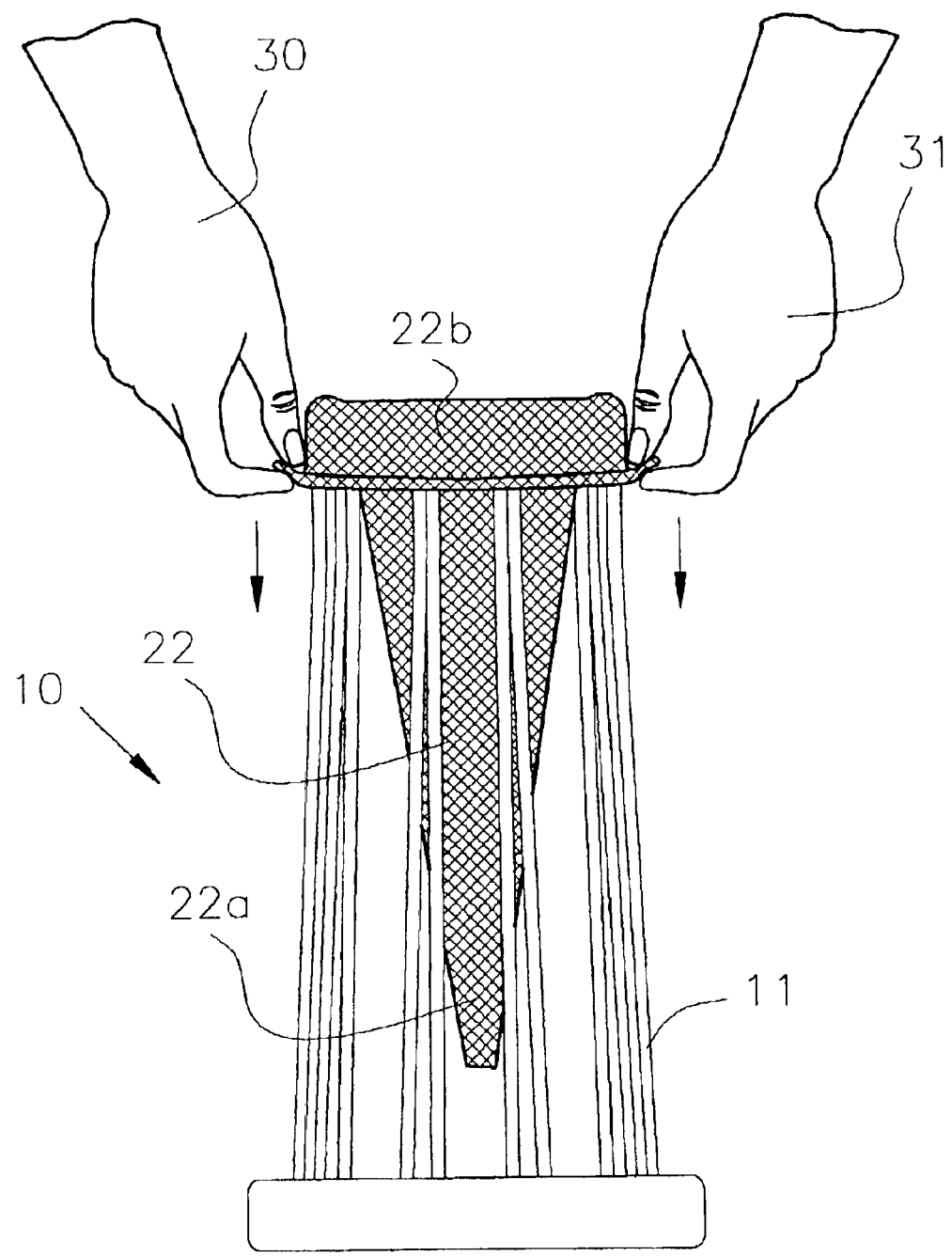
FIG. 10 is an elevational view of the device showing the first step in the deployment of a compression bandage.

FIGS. 3–5 show lock pin means 13 located between each rod 11. Section line B—B axially intersects lock pin 11b and hole 11c and perpendicularly intersects rods 11. The combination of pins 11b and holes 11c form a positive location and locking means for the movement of rods 11 one against the other. FIG. 5 shows the displacement 20 of rod 11, shown as bend 21, in its vertical position. Flat 11a is drilled with hole 13. Locking pin 11b FIG. 10 shows left hand 30 and right hand 31 inserting a bandage 22 into unit 10. The cuff end 22b of bandage 22 is distended to fit over unit 10. Lower cuff end 22a is now opening for deployment. The bandage 22 is then slid downwardly to a point where lower cuff 22a is near the top end.

Figure 12:
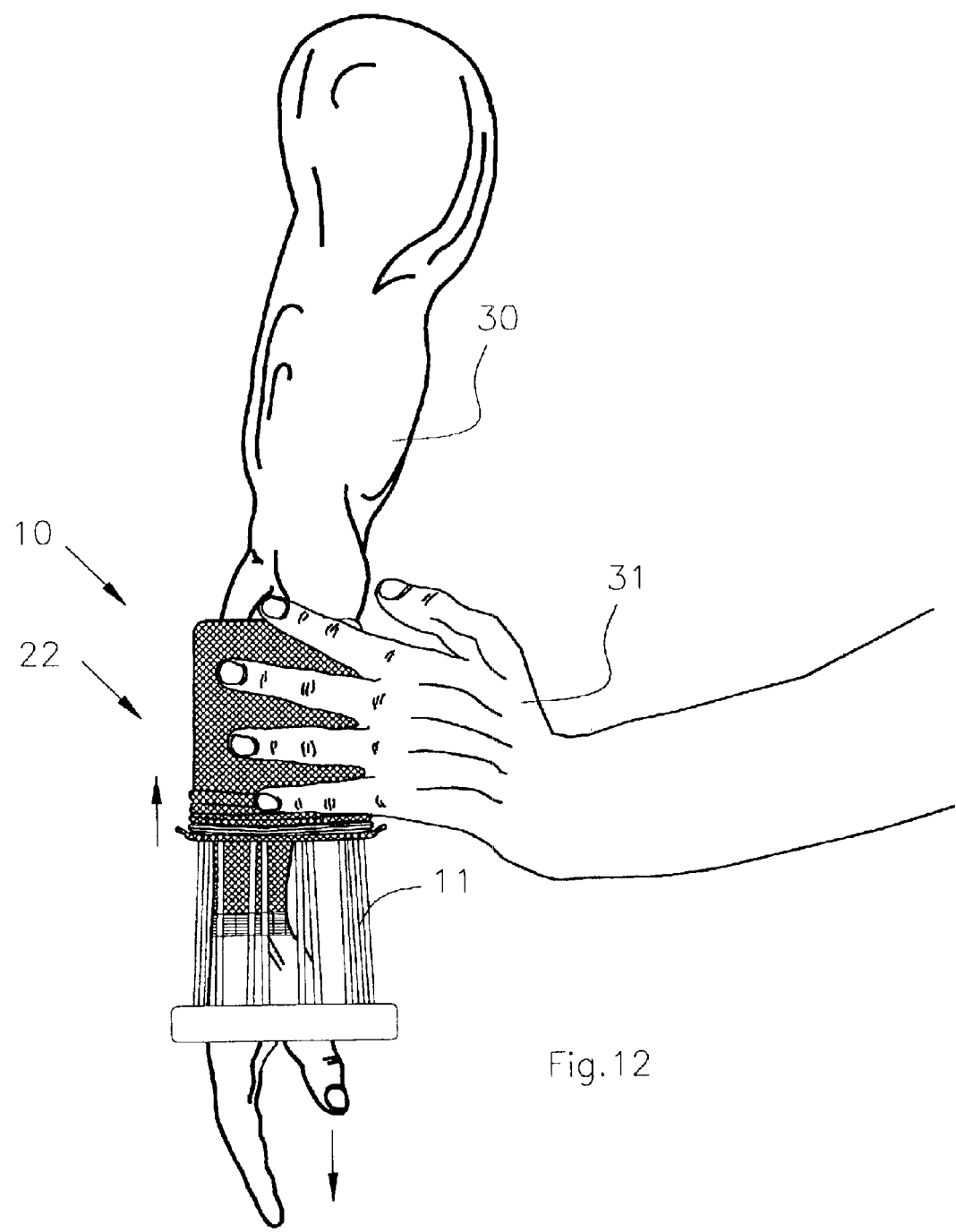
FIG. 12 is an elevational view of the device showing the third step in the deployment of a compression bandage.

FIG. 12 shows the bandage 22 after the arm 30 is inserted into lower cuff end 22a. Lower cuff end 22a is now opening for deployment.

Figure 11:
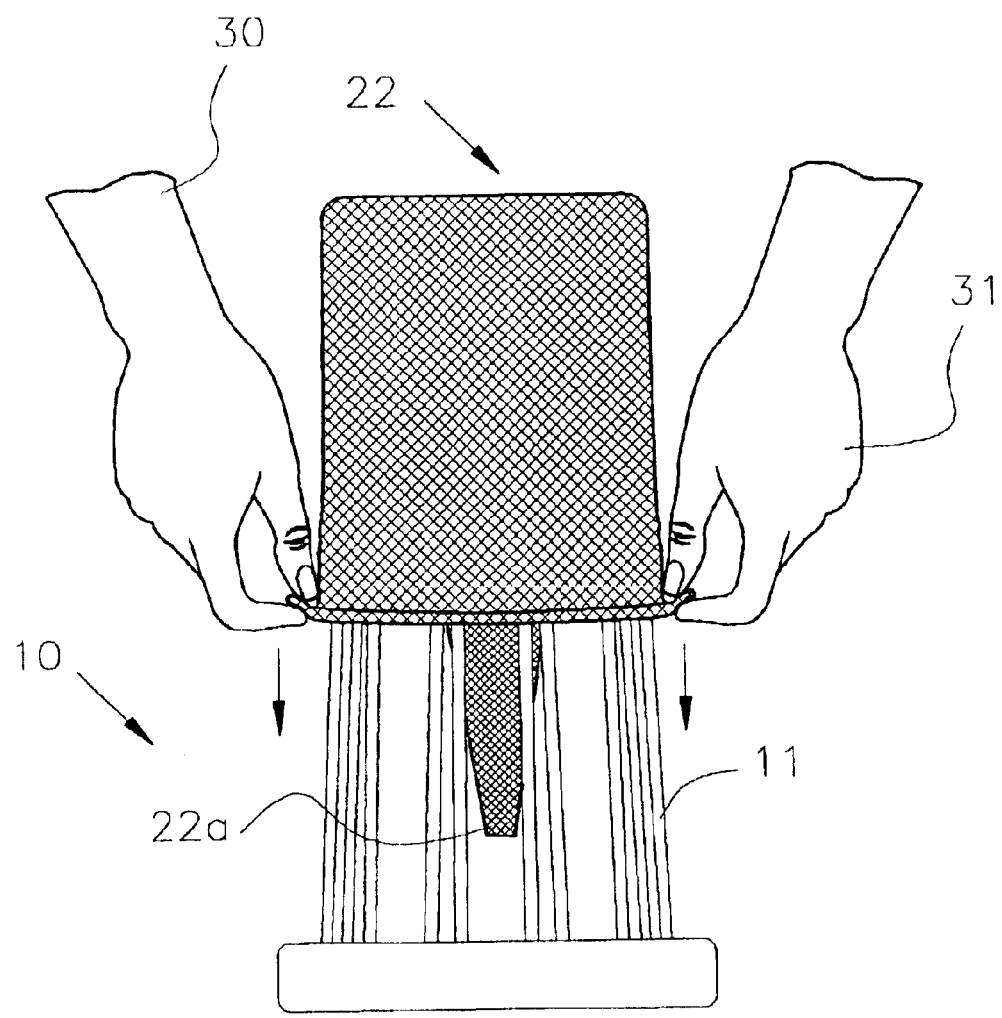
FIG. 11 is an elevational view of the device showing the second step in the deployment of a compression bandage.

In FIG. 11, the bandage 22 is now sufficiently deployed over unit 10 so that (FIG. 12) patient's arm 30 can be pushed through bandage 22 and unit 10 can be simultaneously moved upward by right arm 31.

Figure 13:
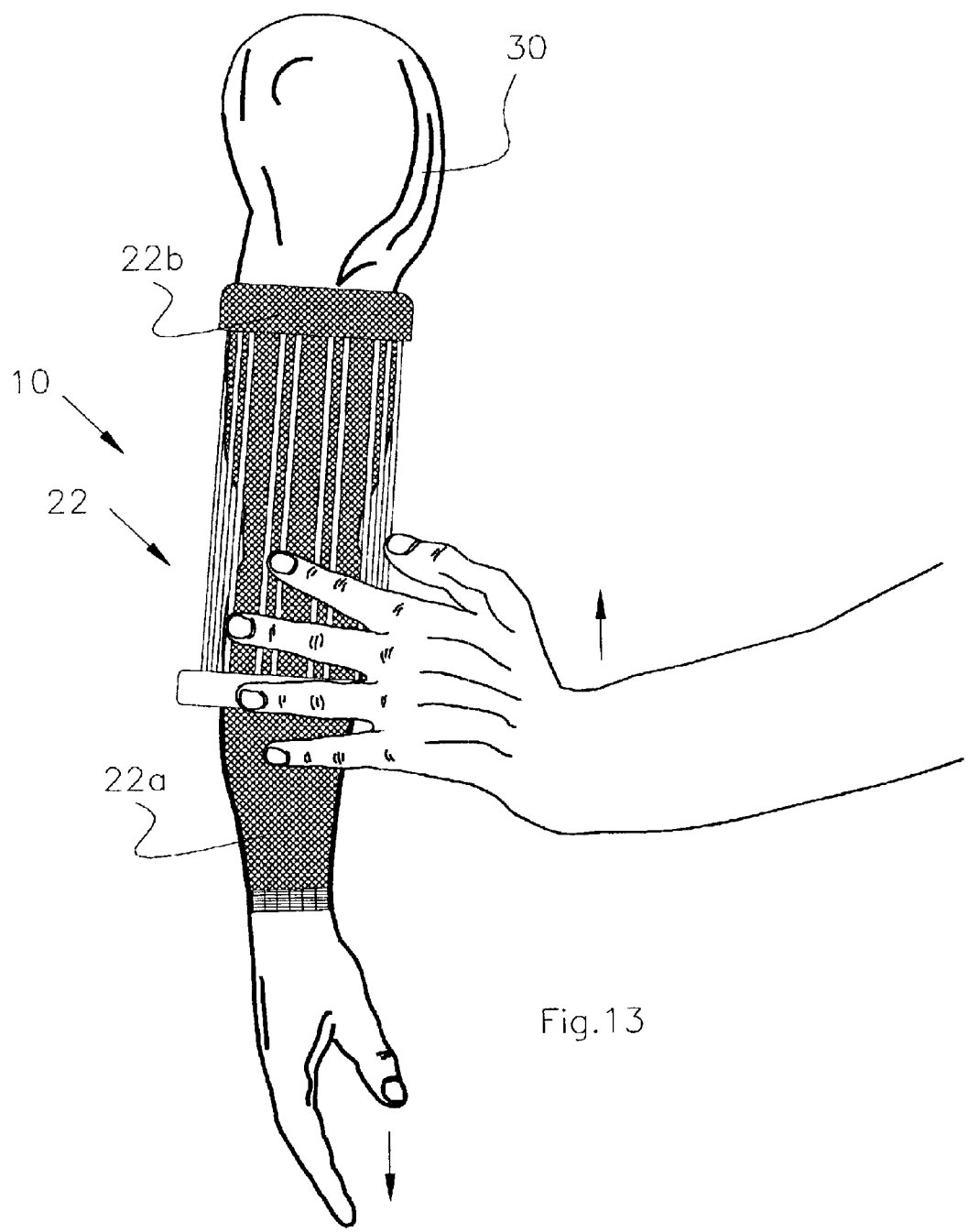
FIG. 13 is an elevational view of the device showing the fourth step in the deployment of a compression bandage.

In FIG. 13, almost fully deployed now, bandage cuff 22b remains expanded by unit 11 allowing it to be closed against left arm 30, whereupon unit 10 can be removed from arm 30.

Figure 14:
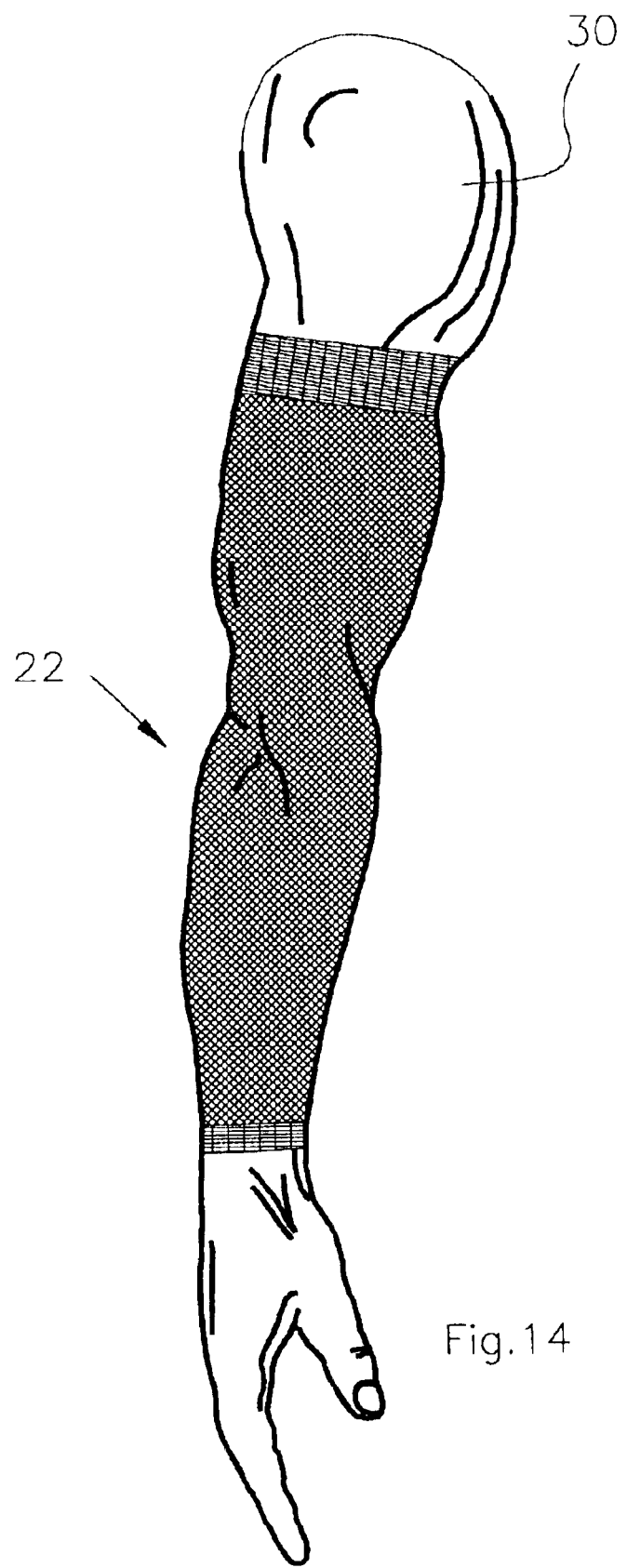
FIG. 14 is an elevational view of the device showing the final deployment of a compression bandage.
Figure 15:
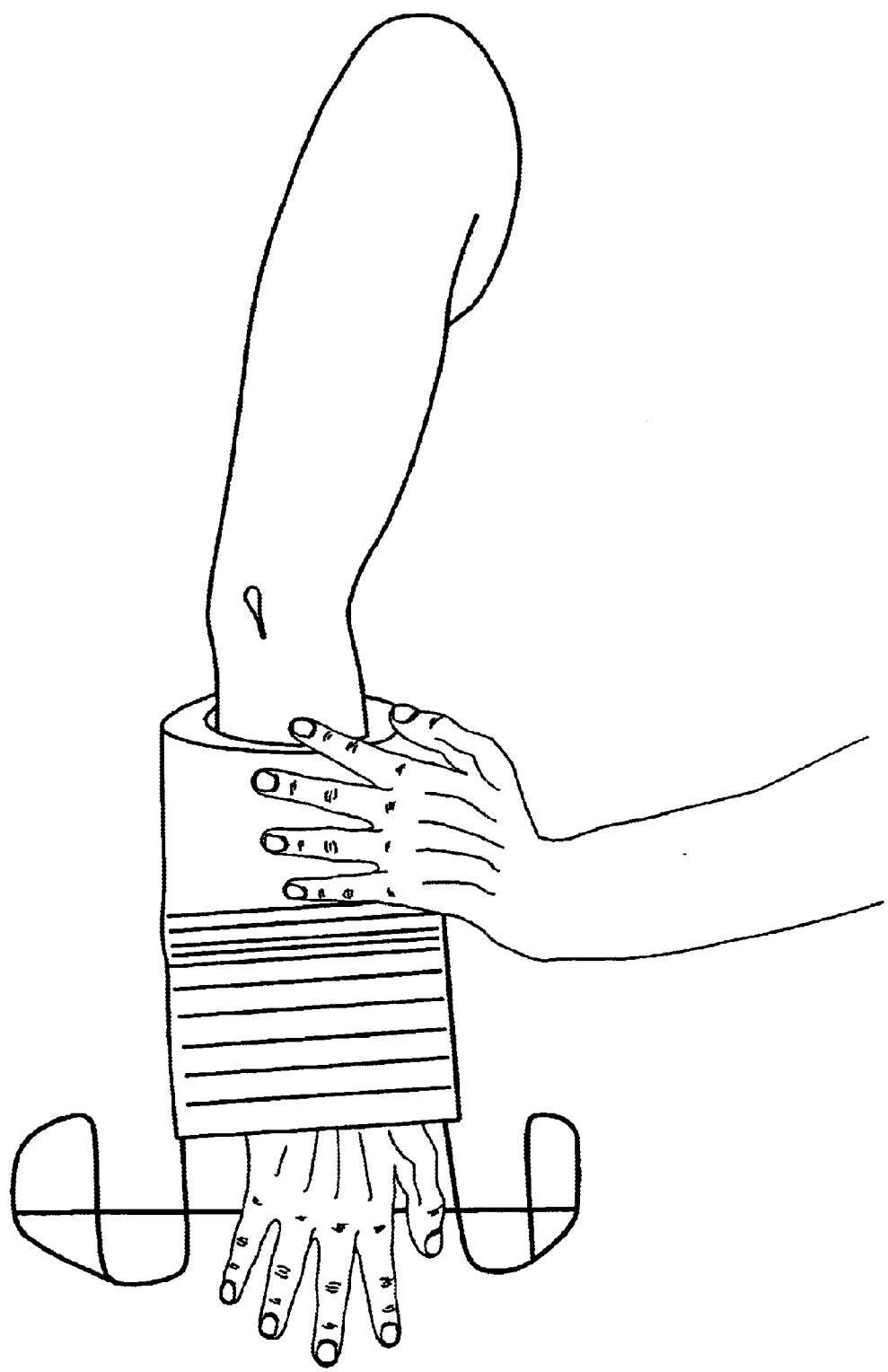
FIG. 15 is a PRIOR ART device.

FIG. 14 shows bandage 22 fully deployed.

What is claimed is:

1. An expandable compression bandage fitting device for deploying bandages over limbs, said device comprising:

an annular base, said base being of such dimension to permit the passage of a limb therethrough, a plurality of rods being generally of an inverted "U" shape, said rods having a proximal end and a distal end, said rods being generally arranged concentrically to said base, said proximal rod ends being attached to said base in a spaced relationship, said distal end forming the top of said "U" shape, a plurality of holes formed in each of said rods near said distal ends, said holes being opposed to each other in adjoining rods, a flat surface formed on each of said rods from a point at the top of said distal ends to a bend formed in said distal end, said bend being located a measured distance from said top of said distal end, and a single lock pin being inserted in a single hole formed in each of said rods, said lock pin engaging the opposed hole in the adjacent rod, thereby forming a rigid structure for deploying said compression bandage.

2. An expandable compression bandage fitting device of claim 1, having a guide being of such circumferential dimension to align said distal ends of said rods, engaging thereby, said lock pins in said holes.

* * * * *